(12) United States Patent
Eschmann et al.

(10) Patent No.: US 10,293,014 B2
(45) Date of Patent: May 21, 2019

(54) **IMMUNE STIMULATING COMPOSITION COMPRISING AN EXTRACT OF *ARONIA* SP. IN COMBINATION WITH SELENIUM AND/OR ZINC**

(71) Applicant: Ursapharm Arzneimittel GmbH, Saarbrucken (DE)

(72) Inventors: Klaus Eschmann, Kleinblittersdorf (DE); Josef Beuth, Cologne (DE)

(73) Assignee: Ursapharm Arzneimittel GmbH, Saarbrucken (DE)

(*) Notice: Subject to any disclaimer, the term of this patent is extended or adjusted under 35 U.S.C. 154(b) by 193 days.

(21) Appl. No.: 14/600,837

(22) Filed: Jan. 20, 2015

(65) Prior Publication Data

US 2015/0132418 A1    May 14, 2015

Related U.S. Application Data

(62) Division of application No. 13/320,021, filed as application No. PCT/EP2010/056190 on May 6, 2010, now abandoned.

(30) Foreign Application Priority Data

May 12, 2009 (EP) ..................... 09006414

(51) Int. Cl.
| | | |
|---|---|---|
| *A61K 33/04* | (2006.01) | |
| *A61K 9/28* | (2006.01) | |
| *A61K 9/08* | (2006.01) | |
| *A61K 9/48* | (2006.01) | |
| *A61K 33/30* | (2006.01) | |
| *A61K 36/73* | (2006.01) | |
| *A61K 45/06* | (2006.01) | |
| *A61P 37/02* | (2006.01) | |
| *A61P 37/08* | (2006.01) | |

(52) U.S. Cl.
CPC .............. *A61K 36/73* (2013.01); *A61K 33/04* (2013.01); *A61K 33/30* (2013.01); *A61K 45/06* (2013.01); *Y02A 50/411* (2018.01)

(58) Field of Classification Search
None
See application file for complete search history.

(56) References Cited

U.S. PATENT DOCUMENTS

| | | | | |
|---|---|---|---|---|
| 5,300,288 A * | 4/1994 | Albright | ............. | A61K 31/785 424/78.08 |
| 6,514,531 B1 * | 2/2003 | Alaux | ................ | A61K 9/2081 424/451 |
| 2006/0093685 A1* | 5/2006 | Mower et al. | ............... | 424/758 |
| 2007/0116838 A1 | 5/2007 | Prakash et al. | | |
| 2007/0269576 A1* | 11/2007 | Barton | ..................... | A23L 2/02 426/599 |
| 2008/0292607 A1 | 11/2008 | Mazzio et al. | | |

FOREIGN PATENT DOCUMENTS

| | | | | |
|---|---|---|---|---|
| DE | 102004029887 A1 * | 1/2005 | .......... | A23L 33/105 |
| DE | 10 2005 046474 A1 | 1/2007 | | |
| JP | 2005-213242 A | 8/2005 | | |
| RU | 2236244 C2 | 9/2004 | | |
| WO | WO 01/15553 A1 | 3/2001 | | |

OTHER PUBLICATIONS

Vunta et al., Mol. Nutr. Food Res. 52: 1316-1323 (2008).*
ATCC RAW 261.7 product sheet, downloaded from ATCC.org, Aug. 8, 2015.*
ATCC DMEM product sheets, downloaded from ATCC.org, Aug. 8, 2015.*
Wightman, Chp. 10, Nutraceutical Beverages, pp. 123-132 (2003).*
Sobieszczyk, "Urinary Tract Infections" (2009) downloaded from http://www.columbia.edu/itc/hs/medical/pathophys/id/2009/utiNotes.pdf on Aug. 8, 2015.*
Wu et al., Journal of Agricultural and Food Chemistry, 52: 7846-7856 (2004).*
Ho et al., International Journal of Molecular Sciences, 15: 11626-11636 (2014).*
Van Lookeren Campagn et al., Cellular Microbiology, 9: 2095-2102 (2007).*
Paradisi et al., Ricercan in Clinic e in Laboratorio, 9: 47-60 (1979).*
Appel et al., Fitoterapia, 105: 73-82 (2015).*
Johnson et al., Arch Environ Contam Toxicol, 39: 243-50 (2000) (Abstract only).*
Hawkes et al., Biological Trace Element Research, 81: 189-213 (2001).*
Trace Elements: Selenium, https://www.cdc.gov/nutritionreport/99-02/pdf/nr_ch4b.pdf, accesed Mar. 23, 2017.*
Arvilommi et al. (Infection and Immunity, 41: 185-189 (1983).*
Google translation DE 102004029887 A1.*
Google translation DE 102005046474.*
Kay et al., British Journal of Nutrition, 91:933-942 (2004).*
Aronia extract of Kay https://web.archive.org/web/20040404145700/http://www.artemis-international.com/standard.html.*
Ohgami et al. IOVS, 46: 275-281 (Year: 2005).*
Zamamiri-David et al., Free Radical Biology and Medicine, 32: 890-897 (Year: 2002).*
Pure Formulas, DHEA in DMSO 5 mg Sublingual Liquid, accessed at https://www.pureformulas.com/dhea-in-dmso-5-mg-sublingual-liquid-14-ml-by intensive-nutrition.html#, (Year: 2018).*
Ito et al., Natural Medicines, 59: 52 (Year: 2005).*
Szopa et al., Eur Food Res Technol, 243: 1645-1657 (Year: 2017).*
Pugh et al., Int. Immunopharmacol., 8: 1023-1032 (Year: 2008).*
Williams, "Investigation of alveolar macrophage function using lucigenin-dependent chemiluminescence", Thorax, 1981, 36, 866-869 (Year: 1981).*

(Continued)

*Primary Examiner* — Robert T. Crow
*Assistant Examiner* — John P Nguyen
(74) *Attorney, Agent, or Firm* — Knobbe, Martens, Olson & Bear LLP

(57) ABSTRACT

Disclosed is a composition which comprises a combination of *Aronia* extract in an amount of at least about 10 µg/mg and seleniumin in an amount from about 0.0001 µg/mg to about 2.0 µg/mg. The composition may further comprise zinc as additional micronutrient. The composition may be formulated as a pharmaceutical or a nutraceutical composition.

6 Claims, 2 Drawing Sheets

(56) References Cited

OTHER PUBLICATIONS

Jalcova, "Effect of heavy metal intoxication on macrophage metabolic activity of mice infected with Ascaris suum", Helminthologia, 51, 3:171-180, 2014 (Year: 2014).*
Speer, "Enhanced Release of Oxygen Metabolites by Monocyte-Derived Macrophages Exposed to Proteolytic Enzymes: Activity of Neutrophil Elastase and Cathepsin G1", The Journal of Immunology,133,4, 2151-2156, 1984 (Year: 1984).*
Gasiorowski K. et al. 2000 "Evaluation of the immunomodulatory activity of four compounds exerting antimutagenic effects on human lymphocytes in vitro" *Cellular & Molecular Biology Letters* 5: 469-481.
Hoffmann, P.R. et al. 2008 "the influence of selenium on immune responses" *Mol Nutr Food Res* 52: 1273-1280.
Kohn, M. 2003 "The State of CAM in UK Cancer Care: Advances in Research, Practice and Delivery" The NCI Office of Cancer Complementary and Alternative Medicine Invited Speaker Series (in 41 pages).
Kulling, S.E. et al. 2008 "Chokeberry (*Aronia melanocarpa*)—A review on the characteristic components and potential health effects" *Planta Med* 74: 1625-1634.
Overbeck, S. et al. 2008 "Modulating the immune response by oral zinc supplementation: a single approach for multiple diseases" *Arch Immunol Ther Exp* 56: 15-30.
Rooprai, H.K. et al. 2003 "The potential for strategies using micronutrients and heterocyclic drugs to treat invasive gliomas" *Acta Neurochir* 145: 683-690.
Tulev et al. 2004 "Immunotropic preparation Vitulin B" Chem Abstracts Service, Columbus, Ohio, Database Accesion No. 141: 325705 (in 2 pages).
Valcheva-Kuzmanova, S.V. et al. 2009 "Current knowledge of Aronia melanocarpa as a medicinal plant" *Folia Medica, University of Medicine* 48: 11-17.

\* cited by examiner

IMMUNE STIMULATING COMPOSITION COMPRISING AN EXTRACT OF *ARONIA* SP. IN COMBINATION WITH SELENIUM AND/OR ZINC

FIELD OF THE INVENTION

The present invention relates to an immune stimulating agent, and relates in particular to a composition comprising *Aronia* extract and selenium for stimulating the immune system, and pharmaceutical or nutraceutical compositions comprising the same.

BACKGROUND

*Aronia* (chokeberry) is a deciduous shrub which belongs to the plant family Rosaceae. Within the genus *Aronia* several species and hybrids are known, such as *Aronia melanocarpa* (black chokeberry), *Aronia arbutifolia* (red chokeberry), and *Aronia* x *prunifolia* (purple chokeberry). The *Aronia* fruits are small pomes and the juice of it is known to be astringent and to have a high content of vitamin C and other antioxidants.

Due to their intensive fruit color *Aronia* is used as a coloring agent for beverages and other food products, as disclosed e.g. in U.S. Pat. No. 6,703,056, WO 2005 058052, and WO 2006 138419. Beside this, the *Aronia* fruits have awaken interest due to their antioxidative qualities. For example *Aronia melanocarpa* is known to have high contents of phenolic compounds, especially anthocyanins, which are mainly located in the skin of the berries for UV protection of the pulp and the seeds. These anthocyanins give *Aronia melanocarpa* an extraordinary antioxidative strength. A parameter showing the capacity of a compound or an extract to deal with oxidative stress is the oxygen radical absorbance capacity or ORAC. *Aronia* shows high ORAC values and is therefore also used/added as a functional food or nutraceutical. For example, US 2007 0020358 discloses a sports drink concentrate which may include *Aronia* as a nutraceutical ingredient. A functional sweetener composition comprising an *Aronia* extract as antioxidant is disclosed in WO 2007 06 1900, and WO 2007 076857 teaches a chewing gum composition containing *Aronia* which is used as a source of antioxidants.

Further thereto, it is known from the prior art that *Aronia* or compounds thereof may be used for the preparation of pharmaceutical compositions or nutraceutical compositions and food supplements. For example DE 10 2004 029 887 A1 discloses a dietary supplement on the basis of pomace comprising an extract of the skin of *Aronia* fruits which dietary supplement is described to have a high radical protection factor. DE 10 2004 052 882 A1 teaches a dietary supplement on the basis of a specific selection of fruit and legume concentrates, which comprises inter alia an *Aronia* fruit juice concentrate. Said dietary supplement is described to strengthen the immune system, wherein it is set forth that the combination of ingredients synergistically influences the impact of the ingredients.

WO 2001 015553 teaches that food supplements containing *Aronia* fruit extract may be used to inhibit an inflammation mediated by cyclooxygenase, i.e. it is disclosed that *Aronia* extracts have an anti-inflammatory activity due to an inhibition of COX-2 activity preferentially over COK-1 activity.

DE 10 2005 046 474 A1 teaches to use an extract of the fruit's skin of *Aronia* sp. for the prophylactic and therapeutic treatment of bacterial, mycotic and/or inflammatory diseases/conditions. The effect achieved is attributed to an antibacterial and antimycotic effect of said extract. A direct influence of the extract on the immune system is not disclosed.

In addition thereto, WO 2002 005827 teaches the use of *Aronia* extract for the preparation of a medicament for the treatment of brain cancer and further discloses a nutraceutical composition for the treatment of cancer comprising one or more flavonoids from *Aronia* and the micronutrients selenium and zinc.

Micronutrients are needed and involved, e.g. as cofactors for enzymes, in a plurality of metabolism processes and are therefore important ingredients in food. Accordingly, and as taught by the prior art, micronutrients may be added to different kinds of food for example to functional food in order to achieve or improve certain physiological functions.

As regards the immune system, it is known that the micronutrients selenium and zinc affect beside other physiological functions the immune status. Selenium is known to be required for a proper activity of neutrophils, macrophages, NK cells, T lymphocytes and some other immune mechanisms and an insufficient supply of selenium to the human body may result in a weakened immune system. Zinc is known to be an important ion for enzymes, proteins and transcription factors, and is therefore involved in many functions of the body also including immune responses.

As already indicated above, combinations of an *Aronia* extract with at least one micronutrient, in particular with selenium and/or zinc, are known from the prior art. However, this often seems to be a "combination by chance". For example WO 2005 058052 and WO 2006 138419 teach the use of *Aronia* as a coloring agent, while zinc and selenium are comprised in a stabilizing mixture for the food product taught in these references. In other cases, the combination of *Aronia* extract with selenium and/or zinc as taught in the prior art may be considered just as a consequence of the purpose of the product. For example, the sports drink as disclosed in US 2007 0020358 teaches to use *Aronia* due to its high ORAC value, while selenium and zinc are added as micronutrients. Hence, these components are not taught in the prior art to be combined in order to achieve a certain effect, which results from the interrelated action of these components. In particular, the prior art does not seem to indicate that due to the selective combination of an *Aronia* extract with selenium and/or zinc, a composition having an improved immune stimulating effect may be obtained.

Even if different kinds of immune stimulating agents are known, there is an ongoing need for improved immune stimulating agents, since especially due to the increasing environmental stress of modern life the immune system of human beings is continuously exposed to various kinds of stress. Often agents based on a natural or biological basis are preferred to synthetic pharmaceutical products, because they are on the one hand often better accepted from the patient or the consumer and may be also manufactured in a more cost effective way, especially in the case when a plant extract may be used per se, since no chemical synthesis and/or purification of effective compounds is necessary.

Therefore, it is clear from the above that there is a need for improved substances or compositions having immune stimulating effects.

SUMMARY OF THE INVENTION

In the lines of extensive studies leading to the present invention the inventors have found that particular micronutrients, namely selenium, either alone or in combination with zinc, has an advantageous effect on the beneficial effects of *Aronia* extracts. It has been surprisingly found that an *Aronia* extract to which a particular amount of selenium or selenium and zinc has been added increases the macrophage activity by far in comparison to a composition merely containing a natural *Aronia* extract. The increased macrophage activity renders the present composition particularly suitable for the treatment of inflammatory diseases or conditions, bacterial infections, fungal infections, viral infections, parasitic infections.

Hence the above problem has been solved by providing a composition comprising an *Aronia* extract in an amount of at least about 10 µg/mg and selenium in an amount of from about 0.0001 µg/mg to about 2.0 µg/mg. It will be appreciated in this context that according to the present invention selenium is added to the *Aronia* extract. In other words, the amount of selenium or the combination of selenium and zinc is beyond the natural fluctuation range in an *Aronia* extract.

According to one embodiment the composition further comprises additional zinc, preferably in a concentration from about 0.0001 mg/mg to about 0.5 mg/mg.

According to another embodiment the composition further comprises at least one pharmaceutically or nutraceutically acceptable excipient or a mixture thereof.

According to yet another embodiment the composition is formulated as a pharmaceutical composition, preferably designed for oral, such as peroral, buccal, sublingual, mucosal, or topical administration.

According to yet another embodiment the composition is formulated as a nutraceutical or supplementary neutraceutical composition, preferably in the form of an ingestible solution or suspension, comprising the active ingredient in dissolved or suspended form, or as a solid administration form, such as in the form of tablets, capsules, dragees, or added as a food supplement to daily food products.

According to a further embodiment the composition according to the present invention is for the preparation of a medicament, preferably for the treatment of inflammatory diseases or conditions, bacterial infections, fungal infections, viral infections, parasitic infections and combinations thereof. The inflammatory disease or condition is preferably associated with autoimmune diseases, inflammatory bowel disease, multiple sclerosis, scleroderma, and graft-versus-host disease.

DETAILED DESCRIPTION OF CERTAIN ILLUSTRATIVE EMBODIMENTS

Figure 1:
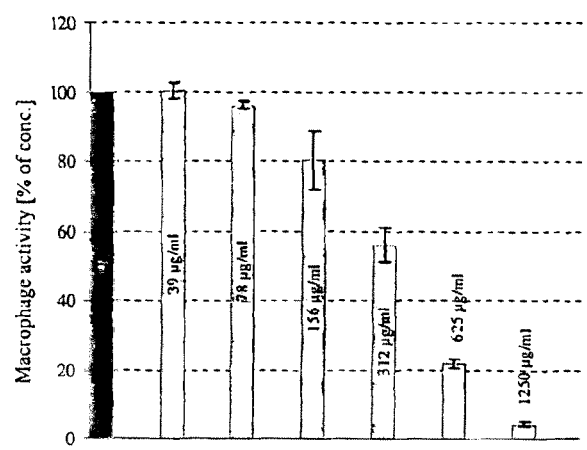
FIGS. 1 and 2 shows evaluation of the optimal concentration of *Aronia* extract on macrophage activity of macrophages of the mouse leukaemic monocyte macrophage cell line RAW 264.7. It may be seen that concentrations above approx. 40 µg/ml decrease macrophage activity.
Figure 2:
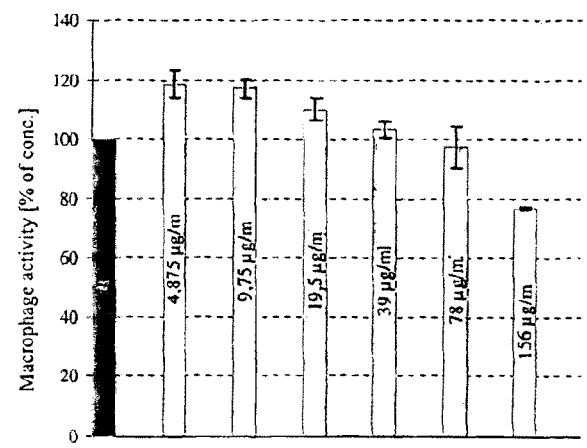
Figure 3:
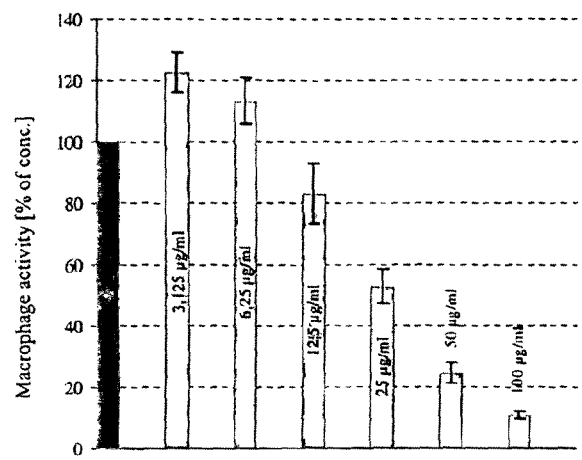
FIG. 3 shows the immune stimulatory activity of selenium employing macrophages of the cell line RAW 264.7. It may be seen that concentrations above approx. 8 µg/ml decrease macrophage activity.
Figure 4:
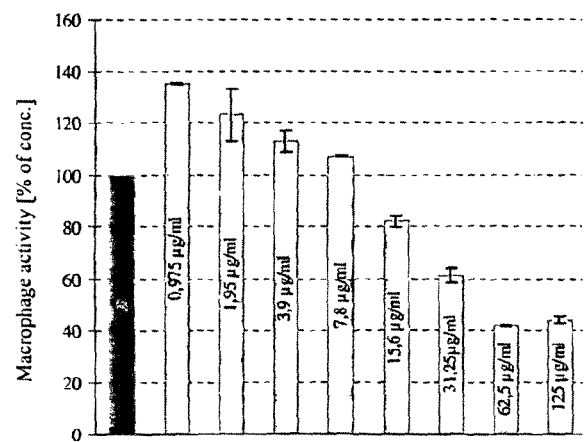
FIG. 4 shows the immune stimulating effect of a composition according to the present invention by means of the activity of macrophages of the cell line RAW 264.7 in dependence from the added selenium concentration. The composition comprises an *Aronia* extract in a concentration of 4.875 µg/ml.

The present invention discloses a composition which comprises a combination of an *Aronia* extract and the micronutrient selenium. The composition may also comprise zinc as further micronutrient, and is designed/used for stimulating the immune system.

According to the present invention the *Aronia* extract originates from one *Aronia* species which is pharmaceutically and nutraceutically acceptable or is a mixture of different pharmaceutically/nutraceutically acceptable *Aronia* species. *Aronia* species that may be used include, but are not limited to *A. melanocarpa*, *A. arbutifolia*, and *A.* x *prunifolia*. According to a preferred embodiment of the present invention *Aronia melanocarpa* is used.

The *Aronia* extract may be derived from the whole fruit or from parts of the fruit. For example the extract may be produced on the base of the pomace of the fruits. The *Aronia* extracts may be obtained according to any suitable method known by a person skilled in the art. The extract may be based on fresh fruits or dried fruits or fruit juices. If desired, one or more particular active compounds may be selectively enriched in the extract. An *Aronia* extract may be obtained to the general knowledge of the skilled person. Suitable ways for preparing an *Aronia* extract are for example disclosed in DE102004029887 and DE102005046474. It will be, however, appreciated that in principle each preparation of plant extracts may be modified according to general knowledge in order to obtain *Aronia* extracts suitable for the present invention. General extraction methods for isolating plant material is for example disclosed in FR2892933 and Ljubuncic P. et al. (*J. Ethnopharnzacol.*, October 3, 101(1-3) (2005), 153-61).

The *Aronia* extract may be prepared using whole fruits as starting material. The fruits are washed with water of a temperature between 30 and 50° C., preferably of 40° C. and afterwards enzymatically treated with e.g. an inulinase, preferably fructozyme, for partial or complete cell disruption. Suitable enzymes as well as reaction conditions are well known to the skilled person. The residue obtained after pressing is extracted with aqueous potassium sulfite solution (approx. 10-30 w/v) for 1 to 3 hours at room temperature (approx. 21-24° C.). The extract is treated with pectin degrading enzymes, such as pectinex or pectinol, at a pH of approx. 3-4, preferably pH 3, for 0.5-2 hours. Afterwards the extract is distilled under vacuum at a temperature of around 40-58° C., preferably 45-50° C., yielding *Aronia* extract having a residual water content of approx. 30-40 w/w.

Alternatively, the *Aronia* extract may be prepared by means of an ethanol extraction or it may be prepared as a dry extract.

The composition according to the present invention comprises the *Aronia* extract in a concentration from at least about 10 µg/mg to about 990 µg/mg, preferably from about 20 µg/mg to about 950 µg/mg. Even more preferred from about 40 µg/mg to about 900 µg/mg. Still more preferred is a concentration in the range from about 50 µg/mg to about 800 µg/mg. Still even more preferred is a concentration from about 60 µg/mg to about 800 µg/mg. Most preferably the *Aronia* extract is concentrated in a range from about 80 µg/mg to about 800 µg/mg.

In a preferred embodiment a fluid composition of the present invention comprises *Aronia* extract in a concentration of about 10 µg/mg to about 200 µg/mg, more preferred about 60 µg/mg to about 150 µg/mg and most preferred about 80 µg/mg.

In another preferred embodiment a solid or dried composition of the present invention comprises *Aronia* extract in a concentration of about 100 µg/mg to about 990 µg/mg, more preferred from about 300 µg/mg to about 800 µg/mg, even more preferred from about 400 µg/mg to about 700 µg/mg and most preferred about 600 µg/mg.

The values given are intended to mean the final concentration of the *Aronia* extract in the composition according to the present invention, i.e. the concentration with which the extract is administered to a patient or a subject in need thereof.

According to the present invention the composition also comprises the micronutrient selenium. According to one embodiment the composition comprises *Aronia* extract and a combination of the micronutrients selenium and zinc. As used herein comprising a micronutrient is intended to mean that additional amounts of said micronutrient(s) is/are added in addition to the micronutrients which may be already present in the *Aronia* extract. The *Aronia* extract, particularly from the species *Aronia melanocarpa*, may contain natural amounts of 4 mg/kg zinc and about 20 µg/kg selenium. It will be appreciated that these natural amounts may vary dependent on the fruits specifies and growth conditions.

A recently performed analysis in a certified laboratory revealed inter alia the following contents of metals in such an *Aronia* extract (accuracy of the values±20%):

TABLE 1

| Metal | Dimension | Amount |
|-------|-----------|--------|
| selenium | mg/kg | <0.03 |
| zinc | mg/kg | ~4.0 |

The micronutrient(s) selenium or selenium and zinc may be provided for example, but not limited thereto as inorganic salts, such as chlorides, sulfates, and the like, as organic salts and other bioavailable forms, such as amino acid chelates or combinations thereof. As used herein the terms "selenium" and "zinc" are intended to comprise any compound containing selenium and zinc, respectively, including salts, complexes or other forms of said micronutrients, also including elemental selenium or zinc. Acceptable forms of selenium and zinc are well known to the skilled person. In case of given concentrations or ranges of concentrations of said micronutrients said values are intended to indicate the concentration of selenium or the selenium ion, and the concentration of zinc or the zinc ion, respectively.

For example, but not limiting the present invention thereto selenium may be provided as selenomethionine, elemental selenium, various selenium salts, such selenium chloride, and selenium yeast or combinations thereof. According to a preferred embodiment of the present invention selenium is provided as selenium yeast or sodium selenite/sodium selenate.

For example, but not limiting the present invention thereto zinc may be provided as zinc acetate, zinc ascorbate, zinc chloride, zinc citrate, zinc gluconate, zinc lactate, zinc sulphate, amino acid chelated zinc, or combinations thereof. According to a preferred embodiment of the present invention zinc is provided as zinc chloride.

The composition according to the present invention may be provided in liquid form or in dried/solid form, e.g. in a lyophilized form. According to a preferred embodiment of the present invention the composition is provided in a sterile form.

During the extensive studies leading to the present invention, it has been surprisingly found that a composition comprising an *Aronia* extract and additionally added selenium or additionally added selenium and zinc has an enhanced immune stimulating effect in comparison to the single compounds of the composition according to the present invention. Without wishing to be bound to any theory it seems that the beneficial immune stimulating effect of the composition according to the present invention is based on a synergistic effect of the complex mixture of compounds comprised in the *Aronia* extract in combination with the additionally added selenium. A further synergistic effect may be achieved when adding zinc to the composition comprising *Aronia* extract and selenium.

In particular, the composition according to the present invention has been shown to increase the macrophage activity. Macrophages belong to the innate immune system which is e.g. responsible for destroying virus infected cells, parasites and tumour cells. Macrophages represent matured monocytes, which in turn belong to the white blood cells. Macrophages phagocytose and digest invading microorganisms, even protozoa, debris, foreign bodies as well as damaged, dead and senescent cells.

Accordingly the composition according to the present invention can be used to stimulate the immune system. In particular, the composition according to the present invention may be used for the preparation of a medicament for the treatment of a variety of diseases or conditions which are based on a reduced activity of the immune system, or which may be prevented or treated by stimulating the immune system. In particular, diseases or conditions may be treated or prevented that are based on a reduced macrophage activity or which may be prevented or treated by enhancing the macrophage activity.

Within the present invention treatment is intended to mean prophylactic or therapeutic treatment, wherein the therapeutic treatment may be palliative or curative.

Since the composition according to the present invention is characterized by an immune stimulating activity it may be also used for the preparation of a medicament designed for adjuvant therapy during the treatment of diseases which treatment is beneficially affected by stimulating the immune system. Furthermore, the composition according to the present invention may also be used for the preparation of a dietary supplement for supporting the immune system.

According to one embodiment of the present invention the composition is designed for the treatment of inflammatory diseases or conditions, bacterial infections, fungal infections, viral infections, parasitic infections and combinations thereof.

In particular the composition may be used for alleviate or improving any disorder or disease including but not limited to septic shock, haemodynamic shock, sepsis syndrome, post ischaemic reperfusion injury, inflammatory bowel disease, graft-versus-host disease, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory diseases of the eye, inflammatory bowel diseases such as Crohn's disease and colitis, osteo- and rheumatoid arthritis, ankylosing spondylitis, psoriatic arthritis, adult Still's disease, uveitis, Wegener's granulomatosis, Behcet disease, Sjoegren's syndrome, sarcoidosis, conjunctivitis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. In addition, wound healing may be facilitated.

Examples of bacterial or microbial infections comprise any infection with gram positive or gram negative bacteria. Pathological conditions of microbial infections which can be treated or prevented by the present compositions include, but are not limited to, conditions such as chronic upper respiratory disease, wound infection, osteomyelitis, endocarditis, skin polymicrobial infections, bronchial asthma, chronic sinusitis, cystic fibrosis or acne vulgaris.

Examples of fungal infections include for example blastomycosis, coccidiodomycosis, cryptococcosis, histoplasmosis, sporotrichosis, chromoblastomycosis, lobomycosis, dermatophytosis, dermatomycosis, onychomycosis, piedra, mycetoma, fusariosis, pityriasis versicolor, tinea barbae, tinea capitis, tinea corporis, tinea cruris, tinea favosa, tinea nigra, tinea pedis, phaeohyphomycosis, rhinosporidiosis, aspergillosis, mycotic keratitis, candidiasis.

Viral infections to be treated may be caused by viruses including, but not limited to, lentiviruses such as human immunodeficiency virus types 1 and 2 (HIV), human T-cell lymphotropic virus type 1 and 2 (HTLV-I and HTLV-II), SIV, EIAV (equine infectious anemia virus), BIV, FIV, CAEV, VMV, and MMLV (Moloney murine leukemia virus). Such viral infections can also be caused by hepatitis A virus, hepatitis B virus, hepatitis C virus, hepatitis D virus, hepatitis E virus, hepatitis G virus, human foamy virus, or by human herpes viruses (e.g., herpes simplex virus type-1, herpes simplex virus type-2, herpes simplex virus type-3 (also known as Varicella-zoster virus), herpes simplex virus type-4 (also known as Epstein Barr virus or EBV), herpes simplex virus type-5, herpes simplex virus type-7). Such viral infections can also be caused by influenza viruses (types A, B or C), human parainfluenza viruses, respiratory syncytial virus, smallpox virus (variola virus), monkeypox virus, vaccinia virus, human papilloma virus, human parechovirus 2, mumps virus, Measles virus, Rubella virus, Semliki Forest virus, West Nile virus, Colorado tick fever virus, foot-and-mouth disease virus, Ebola virus, Marburg virus, polyomavirus, TT virus, Lassa virus, lymphocytic choriomeningitis virus, vesicular stomatitis virus, rotavirus, varicella virus, parvovirus, cytomegalovirus, encephalitis viruses, adenovirus, echovirus, rhinoviruses, filoviruses, coxachievirus, coronavirus (such as SARS-associated coronavirus), Dengue viruses, yellow fever virus, hantaviruses, regional hemorrhagic fever viruses, molluscum virus, poliovirus, rabiesvirus, etc.

Examples of parasitic infections include but are not limited to malaria. Parasitic infections may be caused by organisms such as protozoa, helminths, and ectoparasites.

According to the present invention selenium is added as a micronutrient to the composition comprising *Aronia* extract. Selenium is added in one or more suitable form(s) as set forth above.

During the extensive studies leading to the present invention it was surprisingly found that the beneficial effect, i.e. the immune stimulating effect, of selenium which is added to the *Aronia* extract is dependent on the added selenium concentration.

According to the present invention selenium is added to the composition to a final concentration from about 0.0001 µg/mg to about 2.0 µg/mg. Preferably, selenium may be added to the composition in a range from about 0.0005 µg/mg to about 1.0 µg/mg. Even more preferred from about 0.001 µg/mg to about 0.5 µg/mg. Still more preferred is a concentration ranging from about 0.001 µg/mg to about 0.25 µg/mg. Even still more preferred is a concentration ranging from about 0.001 µg/mg to about 0.2 µg/mg. Most preferred is a concentration between about 0.0012 µg/mg to about 0.1 µg/mg.

According to a preferred embodiment a fluid composition of the present invention comprises selenium in a concentration from about 0.0001 µg/mg to about 0.01 µg/mg, more preferably from about 0.0005 µg/mg to about 0.005 µg/mg, most preferably from about 0.0008 µg/mg to about 0.003 µg/mg and even most preferably about 0.0012 µg/mg.

In another preferred embodiment a solid or dried composition of the present invention comprises selenium in a concentration from about 0.001 µg/mg to about 0.5 µg/mg, more preferably from about 0.005 µg/mg to about 0.01 µg/mg, most preferably from about 0.003 µg/mg to about 0.02 µg/mg and even most preferably about 0.01 µg/mg.

The values given are intended to mean the final concentration of added selenium in the composition according to the present invention, i.e. the concentration with which the added selenium is administered to a patient or a subject in need thereof.

The final concentration of selenium added to the composition according to the present invention may be chosen also in view of the daily requirement amounts of selenium. Accordingly, factors like for example the intended way of administration, and the amount/dosage of the composition given per day and subject, may be considered. Such considerations are within the general knowledge of the skilled person.

According to a preferred embodiment of the present invention zinc may be added to the composition comprising *Aronia* extract and selenium, in one or more suitable forms as set forth above, to formulate a composition according to the present invention.

Zinc may be added to the composition of the present invention in a concentration from about 0.0001 mg/mg to about 0.5 mg/mg. Preferably, zinc may be added to the composition in a range from about 0.0005 mg/mg to about 0.1 mg/mg. Even more preferred from about 0.001 mg/mg to about 0.08 mg/mg. Still more preferred is a concentration ranging from about 0.0015 mg/mg to about 0.006 mg/mg. Even still more preferred is a concentration ranging from about 0.002 mg/mg to about 0.04 mg/mg.

The values given are intended to mean the final concentration of the added zinc in the composition according to the present invention, i.e. the concentration with which the added zinc is administered to a patient or a subject in need thereof.

The final concentration of zinc added to the composition according to the present invention may be selected also in view of the daily requirement amounts of zinc. Accordingly, factors like for example the intended way of administration and the amount/dosage of the composition given per day and subject, may be considered. Such considerations are within the general knowledge of the skilled person.

As regards the concentrations with which selenium and zinc are added to the composition according to the present invention, each of the micronutrients may be added in a concentration or a concentration range as given above The composition according to the present invention may be administered by itself, for example in liquid or in solid form, or may be formulated as pharmaceutical composition or as nutraceutical composition.

Said pharmaceutical composition or nutraceutical composition comprises as an active ingredient a composition according to the present invention and at least one pharmaceutically/nutraceutically acceptable excipient or a mixture of pharmaceutically/nutraceutically acceptable excipients. Suitable excipients include, but are not limited to diluents, carriers, disintegrants, binders, glidants, lubricants, coating agents and the like or mixtures thereof, which might be needed for the preparation of final dosage forms. The pharmaceutical or nutraceutical compositions according to the present invention may be prepared by mixing the active ingredient, optionally in combination with other active compounds, with one or more suitable excipient(s) by methods which are well known to the skilled person. Preferably, the pharmaceutical or nutraceutical compositions are prepared under sterile conditions.

The pharmaceutical composition or nutraceutical composition according to the present invention may comprise from about 1% to about 99% by weight of said pharmaceutically acceptable excipient(s), preferably from about 10% to about 95% by weight, and most preferably from about 20% to about 75% by weight.

The selection of one or more appropriate excipient(s) and their respective amounts is within the general knowledge of the skilled person. The excipient(s) may be selected with regard to the intended route of administration.

The pharmaceutical or nutraceutical compositions according to the present invention may be formulated in a variety of ways to be administered to humans and/or animals. The pharmaceutical or nutraceutical composition according to the present invention may be formulated in a liquid form, i.e. for example in the form of solutions, dispersions, emulsions and gels, or in a solid form. The pharmaceutical composition as well as the nutraceutical composition may be designed for immediate release and/or for sustained release. Accordingly, also depot forms of the composition according to the present invention are within the scope of the present invention.

According to one preferred embodiment of the present invention the composition is formulated as a pharmaceutical composition. Said pharmaceutical composition comprises a therapeutically effective amount of a composition according to the present invention together with one or more pharmaceutically acceptable excipient(s). A therapeutically effective amount of a composition according to the present invention is an amount that when administered to a patient or a subject in need thereof is capable of exerting an immune stimulating effect. In particular, said effective amount is capable of increasing the macrophage activity.

By way of example, but without limiting the present invention thereto, a pharmaceutical composition according to the present invention may be formulated for [G/]oral, such as peroral, buccal, sublingual, or mucosal administration, or for topical administration.

According to a preferred embodiment of the pharmaceutical composition of the present invention, said pharmaceutical composition is designed for oral administration. Such a pharmaceutical composition may be designed as an ingestable solution or suspension, comprising the active ingredient in dissolved or suspended form, or as a solid administration form, such as for example tablets, capsules, dragees, powders, granules.

According to another preferred embodiment of the pharmaceutical composition of the present invention, said pharmaceutical composition is designed for topical administration. Topical administration may be achieved for example, but not limiting the present invention thereto, in the form of ointments, creams, lotions, solutions, and elixirs.

Moreover, since the action of the composition according to the present invention is based on a stimulation of the individual's own immune system, said composition may well be used for the preparation of a nutraceutical composition designed for stimulating the immune system, in particular by increasing the macrophage activity. Therefore, and in accordance with another preferred embodiment of the present invention the composition is formulated as a nutraceutical composition.

As used herein, a nutraceutical composition intended to mean a composition that may be considered as food or a food supplement, which is used to improve the diet in order to provide well-being, health benefits and to help to prevent diseases and infections by stimulating the individual's own immune system.

A pharmaceutical/nutraceutical composition according to the present invention comprises an effective amount of a composition according to the present invention together with one or more pharmaceutically/nutraceutically acceptable excipient(s). An effective amount of a composition according to the present invention is an amount that when administered to a subject in need thereof is capable of exerting an immune stimulating effect.

By way of example, but without limiting the present invention thereto, a nutraceutical composition according to the present invention may be formulated for oral, such as peroral, buccal, sublingual, or mucosal administration.

According to a preferred embodiment of the nutraceutical composition according to the present invention, said nutraceutical composition is designed for oral administration. A nutraceutical composition for oral administration may be designed as an ingestable solution or suspension, comprising the active ingredient in dissolved or suspended form, or as a solid administration form, such as in the form of tablets, capsules, dragees.

The nutraceutical composition according to the present invention may be formulated to be added as a food supplement to daily food products. For example, the nutraceutical composition may be added to beverages, cereals, etc.

It will be appreciated that the amount to be administered depends on the subject to be treated taking into account its age, weight and other personal conditions.

The present invention will now be described by way of specific examples which are only for illustration and which are not intended to limit the scope of the present invention. Various modifications and changes can be made without departing from the scope of the present invention which is set forth in the appended claims.

EXAMPLES

Preparation of the *Aronia* Extract

Fresh-frozen *Aronia* fruits (chokeberries) have been used for preparing the *Aronia* extract (botanical species: *Aronia melanocarpa*). The aqueous pressed juice was concentrated to obtain a ratio of fruits to pressed juice concentrate (native) of 8-10 to 1.

Effect of the *Aronia* Extract and *Aronia* Extract with a Micronutrient on Macrophage Activity Cells: Cell line (RAW 264.7, murine macrophages) was purchased from the America Type Culture Collection and cultivated as recommended.

Chemiluminescence Assay: Lucigenine (Sigma Chemicals Co.) was dissolved in Hank's Balanced Salt Solution (HBSS; Gibco Co.) at a concentration of $2 \times 10^{-3}$ M. This stock solution was further diluted in HBSS prior to use. 1 ml cells ($5 \times 10^6$ cells/ml) were incubated with 0.1 ml solution of Aronia extract and Aronia extract together with sodium selenite (dosis kinetics for each component and the combinations as documented in the figures). All these constituents were kept in an incubator (37° C., 5% $CO_2$) for 30 min, then centrifuged at 1200 U/min for 5 min and resuspended in minimal essential medium (MEM, Gibco Co.).

The reaction mixture consisted of a suspension (0.25 ml) at a concentration of $5\times10^6$ PMNL (polymorphonuclear leucocytes)/ml respectively monocytes/macrophages, 50 µl zymosan, and 0.45 ml medium containing $2\times10^{-6}$ M lucigenine. The reaction mixture was kept at 37° C. before chemoluminescence measurements were performed with a Luminometer (Luminoskan 1251, Labsystems) according to manufacturer's instructions (User's Manual 1995).

What is claimed is:

1. A method of stimulating metabolic activity of a macrophage, the method comprising treating the macrophage with about 4.875 µg/ml to about 39 µg/ml of Aronia extract, about 0.975 µg/ml to about 7.8 µg/ml of selenium and at least one pharmaceutically acceptable excipient, wherein the metabolic activity of the macrophage is increased compared to a metabolic activity in an untreated macrophage.

2. The method according to claim 1, wherein the Aronia extract, the selenium and the at least one pharmaceutically acceptable excipient are formulated in a pharmaceutical composition.

3. The method according to claim 2, wherein the pharmaceutical composition is formulated for peroral/ oral, buccal, sublingual, mucosal or topical administration.

4. The method according to claim 2, wherein the pharmaceutical composition is formulated as a nutraceutical or supplementary nutraceutical composition.

5. The method according to claim 3, wherein the pharmaceutical composition is in a form selected from the group consisting of an ingestible solution, an ingestible suspension and a solid administration form.

6. The method according to claim 5, wherein the solid administration form is in the form of tablets, capsules, or dragees.

* * * * *